United States Patent [19]

Castaldi et al.

[11] Patent Number: 5,186,867
[45] Date of Patent: Feb. 16, 1993

[54] SPIRO-INDOLINE OXAZINE COMPOUNDS WITH PHOTOCHROMATIC AND PHOTOSENSITIZING CHARACTERISTICS AND THE PROCESS FOR THEIR PREPARATION

[75] Inventors: Graziano Castaldi, Briona; Pietro Allegrini, San Donato Milanese; Luciana Crisci, Sant'Angelo Lodigiano; Fiorenzo Renzi, Gorgonzola, all of Italy

[73] Assignee: Enichem Synthesis, S.p.A., Palermo, Italy

[21] Appl. No.: 842,800

[22] Filed: Feb. 27, 1992

Related U.S. Application Data

[63] Continuation of Ser. No. 623,219, Dec. 6, 1990, abandoned.

[30] Foreign Application Priority Data

Dec. 12, 1989 [IT] Italy ................. 22660 A/89

[51] Int. Cl.⁵ .......... G02B 5/23; G02F 1/00; F21V 9/04; C07D 265/00
[52] U.S. Cl. .................. 252/586; 252/583; 252/589; 544/71
[58] Field of Search ........... 252/582, 586, 589, 583; 544/71; 359/361

[56] References Cited

U.S. PATENT DOCUMENTS

| | | | |
|---|---|---|---|
| 4,367,170 | 1/1983 | Uhlmann | 252/586 |
| 4,784,474 | 11/1988 | Yamamoto et al. | 252/586 |
| 4,785,097 | 11/1988 | Kwak | 544/71 |
| 4,792,224 | 12/1988 | Kwiatowski et al. | 252/586 |
| 4,816,584 | 3/1989 | Kwak et al. | 252/586 |
| 4,913,544 | 4/1990 | Rickwood et al. | 252/586 |
| 4,931,219 | 6/1990 | Kwiatkowski et al. | 252/586 |
| 4,962,013 | 10/1990 | Tateoka et al. | 252/586 |
| 4,968,454 | 11/1990 | Crano et al. | 252/586 |
| 5,021,196 | 6/1991 | Crano et al. | 252/586 |

FOREIGN PATENT DOCUMENTS

| | | | |
|---|---|---|---|
| 1258681 | 10/1989 | Japan | 544/71 |
| 85/02619 | 6/1985 | World Int. Prop. O. | 544/71 |

OTHER PUBLICATIONS

Tsugio Okudaira, Chemical Abs., vol. 113, No. 12, p. 639, abstract No. 106503h, Bis[spiro(indoinonaphthoxanie)] Compounds as Photochromic Materials with High Heat Resistance.

*Primary Examiner*—Robert L. Stoll
*Assistant Examiner*—Philip Tucker
*Agent, Attorney or Firm*—Hedman, Gibson & Costigan

[57] ABSTRACT

New compounds of the spiro-indoline-oxazine class possessing photochromatic and photosensitizing charecteristics are definable by the general formula (I):

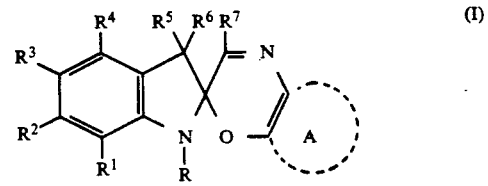

where the substituents R, R¹-R⁷ and A are as defined in the description. The process for preparing the compounds (I) is described, as is their use as photochromic agents able to confer photochromatic characteristics on the articles in which they are incorporated, and as photosensitizing agents.

4 Claims, 3 Drawing Sheets

Graph 1

Graph 2

Graph 3

(VIII) 10(-3) M
▲ deactivated ✶ activated
Graph 1

IA 10(-3)M
▲ deactivated ✶ activated
Graph 2

IB 10(-3)M
▲ deactivated ✶ activated
Graph 3

(VIII) 10(-3)M

Graph 1

VIII+Benzophenone 1:1 10(-3)M

Graph 4

VIII+Anthraquinone 1:1 10(-3)M

Graph 5

Graph 6

Graph 7

SPIRO-INDOLINE OXAZINE COMPOUNDS WITH PHOTOCHROMATIC AND PHOTOSENSITIZING CHARACTERISTICS AND THE PROCESS FOR THEIR PREPARATION

This application is a continuation of Ser. No. 07/623,219, now abandoned, filed Dec. 6, 1990.

This invention relates to new photochromatic compounds and the photochromatic articles which contain them. The invention also relates to the process for preparing these compounds and their use as photosensitizing agents.

Photochromatic compounds are substances having the characteristic of reversibly changing their color and/or degree of light transmission when exposed to certain types of electromagnetic radiation and sunlight, to return to their initial color and light transmission state when the light source is removed. There are many known substances possessing photochromatic characteristics and pertain to various classes of organic and inorganic compounds, as described for example in "Photochromism", G. H. Brown (Ed.), vol. III, of the Weissberger series "Techniques of Organic Chemistry", Wiley Interscience, New York (1971). The most well known photochromatic organic compounds pertain to the spiro-indoline-oxazine class and are able to confer photochromatic characteristics on polymerized organic materials used in solar filters, optical articles, optical memories, printing, photography, fabrics, decorative articles and toys etc., as described for example in U.S. Pat. No. 3,562,172, 3,578,602, 4,215,010 and 4,342,668, and in European patent applications publication Nos. 134,633 and 141,407.

Compared with other known organic photochromatic compounds (such as those of the spiro-pyran class), known photochromatic compounds of the spiro-indoline-oxazine class have the advantage of a much higher fatigue resistance when subjected to repeated coloration and decoloration cycles and a much higher resistance to aging by exposure to sunlight or in artificial aging tests.

However, the organic photochromatic compounds of the known art are practically colorless in their deactivated state, whether in solution in common organic solvents or incorporated into transparent polymer materials, and generally become blue when activated. This blue color is a drawback in its use in photochromatic optical articles, especially in the ophthalmic sector, in which more neutral colours such as grey are preferred. In addition the photochromatic effect obtained is in many cases of little use with regard to transmittance variation in the visible spectrum. In other cases this variation, although satisfactory at low temperatures, is depressed to unacceptably low values as the temperature increases, even if this latter is maintained within the range of values specified for practical use. Finally, spiroindoline-oxazine activation effected under controlled laboratory conditions by irradiation with ultraviolet light of different wavelengths from about 320 to about 380 nm is often not obtained with the same satisfactory speed and intensity when effected by exposure to the frequency spectrum and intensity of sunlight, as required by most uses. Sometimes, by using in association with the photochromatic compound a photosensitizer, as described in "Photochromism", G. H. Brown (Ed.), vol. III, of the Weissberger series "Techniques of Organic Chemistry", Wiley Interscience, New York (1971) and in French patent 2,618,812, greater activation speeds and coloration intensities can be obtained, but without obviating the problems of stability and duration of the photochromatic effect. Examples of such photosensitizers are aromatic compounds (benzene, naphthalene, anthracene) or aliphatic or aromatic ketones (acetone, benzophenone, anthraquinone, xanthone). However in many cases a molecule which acts as a photosensitizer for a photochromatic compound under determined experimental conditions can act as a photoinhibitor if the conditions and/or the photochromatic substrate vary, as reported for example in Journal of the American Chemical Society (1964) 86, page 5687.

The object of the present invention is to overcome the aforesaid drawbacks of the known art by providing new photochromatic compounds of the spiro-indoline-oxazine class.

Figure 1:
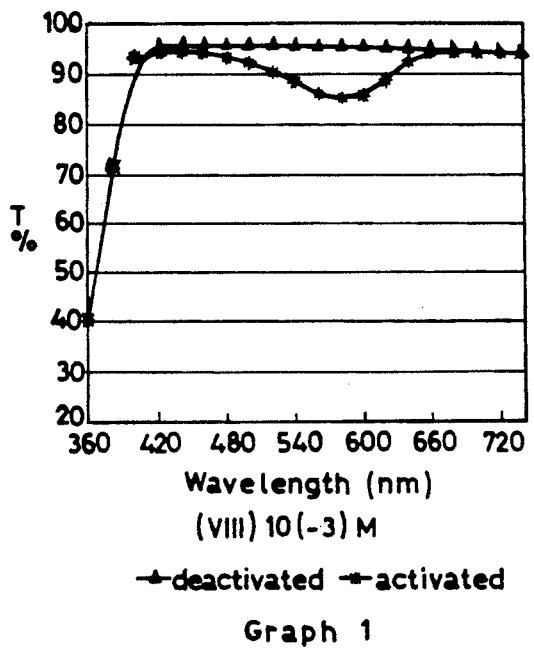
FIGS. 1-3 show the % Transmission of activated and deactivated compounds of the present invention and prior art.
Figure 1:
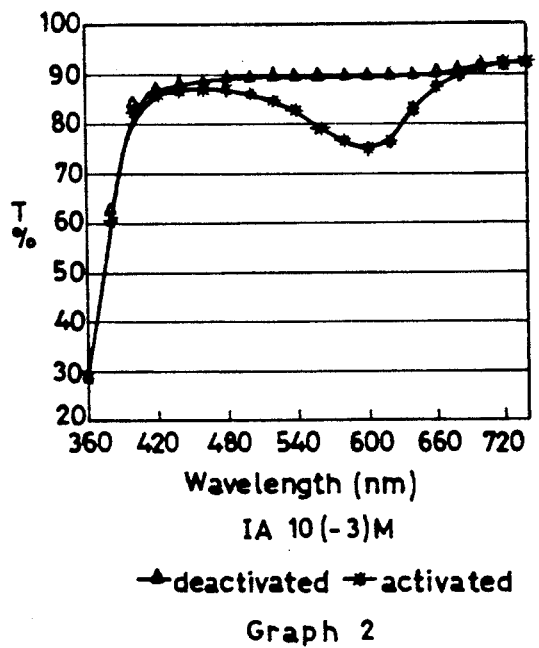
Figure 1:
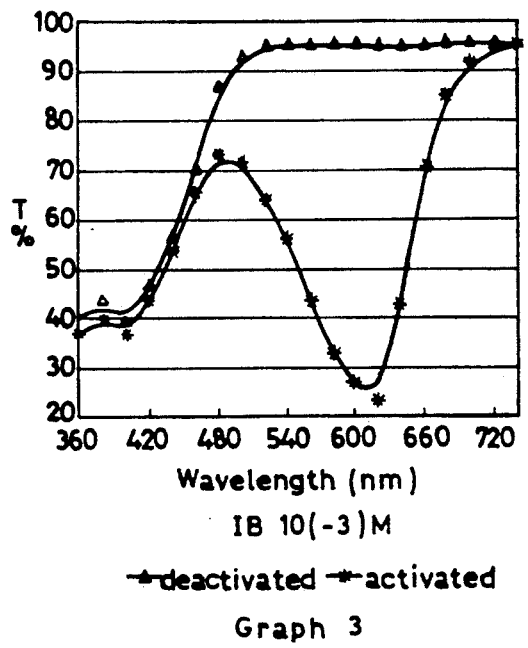

In accordance therewith a first aspect of the present invention is the provision of new photochromatic and photosensitizing compounds of the spiro-indoline-oxazine class definable by the general formula (I):

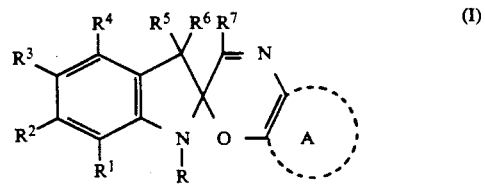

where:

R represents a hydrogen atom; a linear or branched $C_1$–$C_5$ alkyl group; a said $C_1$–$C_5$ alkyl group substituted with 1 to 5 atoms of halogen chosen from fluorine, chlorine, bromine and iodine; hydroxy groups; $C_1$–$C_5$ alkoxy groups; $C_1$–$C_5$ carboxyalkyl groups; cyano groups; a $C_2$–$C_5$ alkenyl group; a phenyl group; or a benzyl group;

$R^1$ to $R^4$, which can be identical or different, each independently represent a hydrogen atom; a linear or branched $C_1$–$C_5$ alkyl group; a said $C_1$–$C_5$ alkyl group substituted with 1 to 5 atoms of halogen chosen from fluorine, chlorine, bromine and iodine, hydroxy groups, $C_1$–$C_5$ alkoxy groups, $C_1$–$C_5$ carboxyalkyl groups, cyano groups; a $C_2$–$C_5$ alkenyl group; a benzyl group; a halogen atom chosen from fluorine, chlorine, bromine and iodine; a hydroxy group; a $C_1$–$C_5$ alkoxy group; an amino group; a $C_1$–$C_5$ monoalkyl amino group; a $C_1$–$C_5$ dialkyl amino group; a $C_3$–$C_{10}$ cycloalkyl amino group; a piperidino, piperazino or morpholino group; a carboxyl group; a $C_1$–$C_5$ carboxyalkyl group; a $C_2$–$C_5$ carboxyalkenyl group; a carboxyamide group; a $C_1$–$C_5$ N-alkyl substituted carboxyamide group; a $C_1$–$C_5$ N,N-dialkyl substituted carboxyamide group; a cyano group; a nitro group; a sulfonic group; a $C_1$–$C_5$ alkylsulfonic group; an arylsulfonic group chosen from benzenesulfonic, p-toluene-sulfonic and p-chlorotoluenesulfonic groups; or an aryl group chosen from phenyl, diphenyl and naphthyl groups;

$R^5$ and $R^6$, which can be identical or different, each independently represent a linear or branched $C_1$–$C_5$ alkyl group; a phenyl group; or $R^5$ and $R^6$, together with the carbon atom to which they are connected, jointly represent a $C_4$–$C_7$ cycloalkyl group;

$R^7$ represents a hydrogen atom; a linear or branched $C_1$–$C_5$ alkyl group; a phenyl group; a halogen atom chosen from fluorine, chlorine, bromine; a $C_1$–$C_5$ alkoxy group; or a phenyl group;

A represents a monocyclic or polycyclic arene group containing at least one C=O carbonyl function on the nucleus or in the side chain, and chosen from those representable by the following formulas (II), (III), (IV), (V) or (VI):

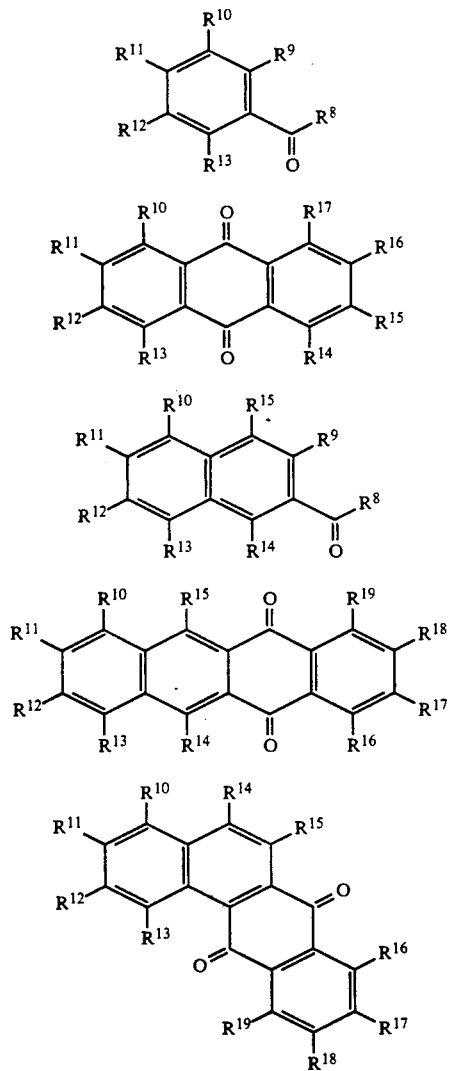

where:

$R^8$ represents a hydrogen atom; a halogen atom chosen from chlorine and bromine; a linear or branched $C_1$–$C_5$ alkyl group; a $C_2$–$C_5$ alkenyl group; a monocyclic or polycyclic aryl group; or a heteroaryl group chosen from phenyl, naphthyl, anthracyl, furanyl, thiophenyl, quinolyl and pyrrolyl; or a said aryl or heteroaryl group substituted with 1 to 4 groups chosen from halogen atoms (fluorine, chlorine and bromine), linear or branched $C_1$–$C_5$ alkyl groups, hydroxy groups, $C_1$–$C_5$ alkoxy groups, nitro groups, cyano groups, amino groups, $C_1$–$C_5$ monoalkyl amino groups; $C_1$–$C_5$ dialkyl amino groups; piperidino groups, piperazino groups or morpholino groups;

two adjacent of $R^{10}$ to $R^{13}$ represent the position of fusion with the oxazine ring in general formula (I), the others having the same meaning as $R^1$–$R^4$;

$R^9$ and $R^{14}$–$R^{19}$ have the same meaning as $R^1$–$R^4$.

In the preferred embodiment, in formula (I):

R represents a methyl, ethyl, benzyl, 2-allyl, 2-hydroxyethyl or 2-carboxymethylethyl group;

$R^1$–$R^4$, identical or different, each independently represent a hydrogen atom, a fluorine, chlorine or bromine atom, or a methyl, isopropyl, trifluoromethyl, hydroxymethyl, benzyl, hydroxy, methoxy, amino, piperidino, morpholino, carboxyl, carboxymethyl, N,N-dimethylcarboxyamide, cyano, nitro or phenyl group;

$R^5$ and $R^6$, identical or different, each independently represent a methyl or phenyl group, or together with the carbon atom to which they are connected they represent jointly a cyclohexyl group;

$R^7$ represents a hydrogen atom, a chlorine atom or a phenyl, methyl or methoxy group;

A is one of the groups of formulas (II) to (VI) in which:

$R^8$ represents a hydrogen atom, or a methyl, isopropyl, phenyl, p-N,N-dimethyl aminophenyl, p-cyano phenyl, p-nitro phenyl, p-methoxy phenyl, naphthyl, 2-thiophenyl, 2-furanyl or 4-pyridyl group;

two adjacent of $R^{10}$–$R^{13}$ represent the position of fusion with the oxazine ring in general formula (I), the others then representing each independently a hydrogen atom, a fluorine, chlorine or bromine atom, or a methyl, isopropyl, trifluoromethyl, hydroxymethyl, benzyl, hydroxy, methoxy, amino, piperidino, morpholino, carboxyl, carboxymethyl, N,N-dimethylcarboxyamide, cyano, nitro or phenyl group;

$R^9$ and $R^{14}$–$R^{19}$ each independently represent a hydrogen atom, a fluorine, chlorine or bromine atom, or a methyl, isopropyl, trifluoromethyl, hydroxymethyl, benzyl, hydroxy, methoxy, amino, piperidino, morpholino, carboxyl, carboxymethyl, N,N-dimethylcarboxyamide, cyano, nitro or phenyl group.

Specific examples of preferred photochromatic compounds according to the present invention are:

1,3,3-trimethyl-8'-oxophenyl-spiro-indoline-2,3'-[3H]naphtho-(2,1-b)-1,4-oxazine (IA);

1,1,1-trimethyl-spiro-indoline-2,3'-[3H]benzo[a]anthracene-7',12'-dione(3,4-b)-1,4-oxazine (IB); and 1,3,3-trimethyl-8'-oxophenyl-6'-piperidinyl-spiro-indoline-2,3'-[3H]naphtho-(2,1-b)-1,4-oxazine (IC).

The compounds (I) according to the present invention can be prepared by reacting a nitroso derivative of the compounds of formula (II), (III), (IV), (V) or (VI), in which two adjacent of $R^{10}$–$R^{13}$ represent one a —N=O group an the other a —$OR^{20}$ group where $R^{20}$ is a hydrogen atom, a metal cation chosen from sodium, potassium, lithium and copper cations; an ammonium or $C_1$–$C_5$ alkylammonium cation; a $C_1$–$C_5$ alkylcarbonyl group; a $C_1$–$C_5$ alkylsulfonyl group or arylsulfonyl group; with a compound of formula (VII):

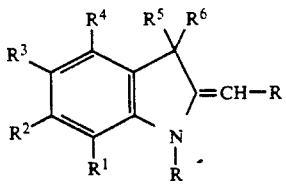

(VII)

where the substituents R and $R^1$-$R^7$ have the aforesaid meaning. The nitroso derivatives of the compounds (II), (III), (IV), (V) and (VI) can be prepared by known methods, such as those described in Organic Synthesis Collective Volume 3, page 411, or in U.S. Pat. No. 3,285,972.

The compounds (VII) can be prepared by known methods, as described for example in Journal American Chemical Society (1941), 63, page 2024; or in Bull. Soc. Chim. Franc. (1968) page 2066.

The reaction is generally conducted by adding the compound (VII) to a solution or suspension of the nitroso derivative of one of the compounds (II), (III), (IV), (V) and (VI), in an inert organic solvent, possibly in the presence of a tertiary amine, operating at a temperature of between 0° and 150° C. and preferably between 0° and 80° C., for a time of between about 1 minute and 24 hours. The inert solvents used in the reaction can be chosen from aliphatic or aromatic hydrocarbons (such as pentane, hexane, heptane, benzene, toluene and xylene); chlorinated aliphatic or aromatic hydrocarbons (such as dichloromethane, 1,2-dichloroethane and chlorobenzene); aliphatic or aromatic ethers (such as diethyl ether, tetrahydrofuran and diphenylether); alcohols (such as methanol, ethanol, isopropanol and n-butanol); ester (such as ethyl acetate); amides (such as dimethylformamide); nitriles (such as acetonitrile); carbonates (such as dimethylcarbonate); and water.

In the reaction the nitroso derivatives of the compounds (II), (III), (IV), (V) or (VI) can be used in quantities varying from 0.1 to 10 moles per mole of the compound (VII), but preferably equimolecular or approximately equimolecular quantities are used. If the reaction is conducted in the presence of a tertiary amine this can be used in a quantity of between 0.1 and 2 moles per mole of the nitroso derivative, but equimolecular or approximately equimolecular quantities are preferably used. Examples of tertiary amines suitable for the purpose are: triethylamine, pyridine, 4-N,N-dimethylaminopyridine, N-methylpiperidine, and N-methylmorpholine.

On termination of the reaction the compounds (I) are isolated by normal methods, for example by evaporating the solvent under vacuum, and then purified for example by crystallization or chromatography. Solvents suitable for crystallization include pentane, hexane, heptane, toluene, ethyl ether, methanol, ethanol, isopropanol, n-butanol, tetrahydrofuran, acetone, methylethylketone, ethyl acetate, dimethylcarbonate, acetonitrile and relative mixtures.

The compounds (I) according to the present invention are crystalline products which are colorless or for example yellow, orange or red in color. Their solutions in the common organic solvents, when not exposed to light sources, are colorless or yellow or yellow-orange in color. When these solutions are exposed to a light source (either visible or ultraviolet) they rapidly assume an intense yellow, yellow-orange, red, blue or green coloration. The coloration falls off rapidly when the light source is removed. The intensity of the coloration observed for solutions of the compounds (I) is much higher, for equal concentrations and experimental conditions, than that of known photochromatic compounds of the spiro-indoline-oxazine class as can be seen from the graphs of FIG. 1.

Specifically, the graphs 1, 2 and 3 of FIG. 1 represent the transmittance curves of $10^{-3}$M toluene solutions of the deactivated form (i.e. before exposure to the light source) and of the activated form (i.e. after exposure to the light source) of a known photochromatic compound (VIII):

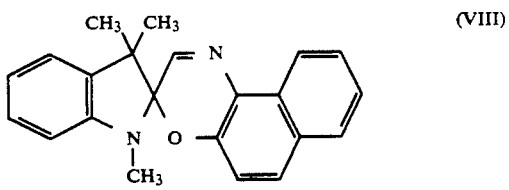

(VIII)

and of the photochromatic compounds (IA) and (IB) of the present invention, the determinations being made by a Macbeth spectrophotometer. Activation is effected by irradiation for 360 seconds with a high pressure mercury lamp.

Figure 2:
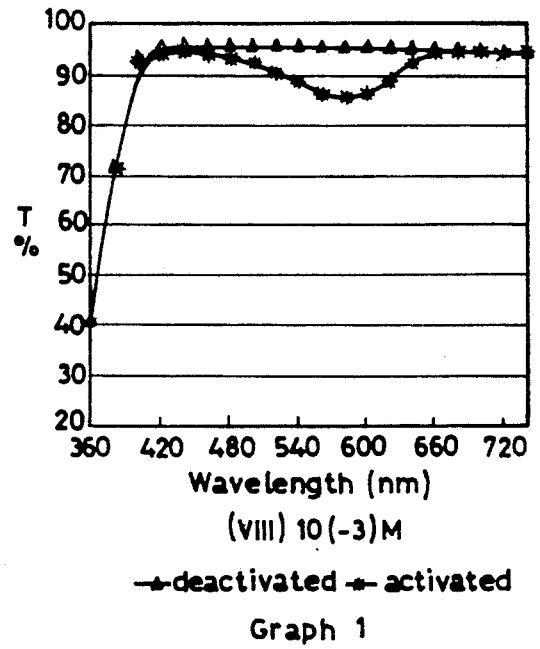
Figure 2:
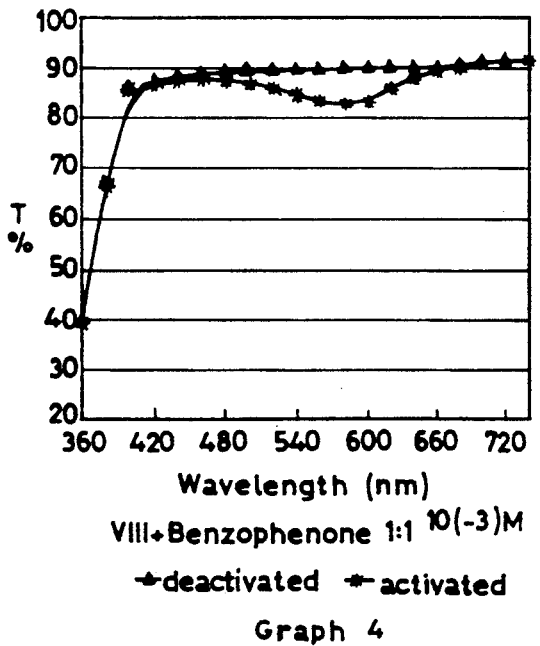
Figure 2:
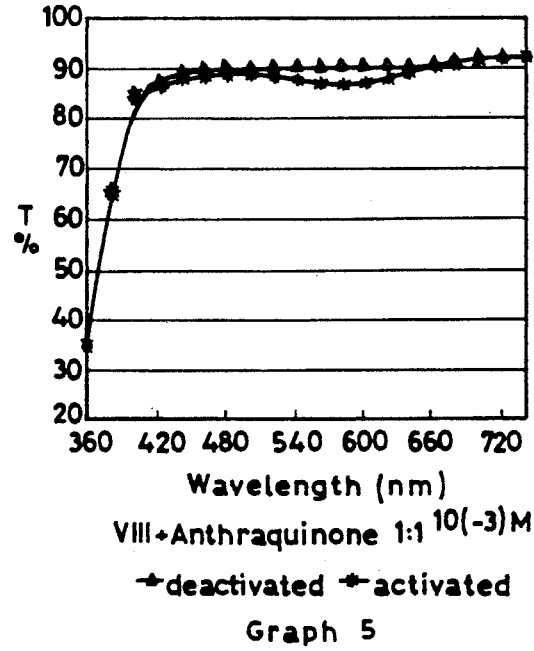
Figure 3:
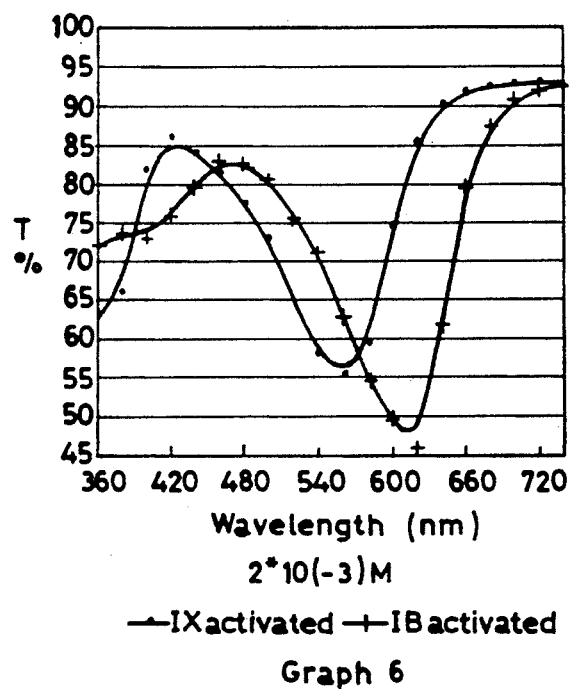
Figure 3:
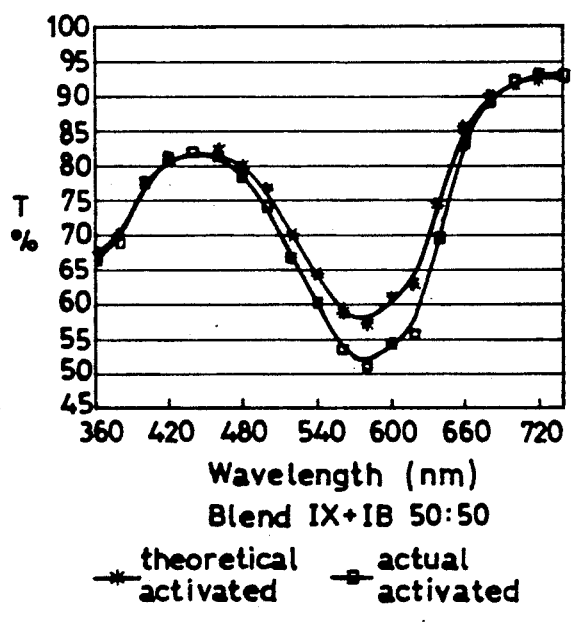

Aliphatic and aromatic ketones are known photosensitizers and/or photoinhibitors, as reported for example in the text "Technologie Photochimique", A. M. Braun, M. T. Maurette, E. Oliveras, Press Polytechniques Romandes, Lausanne (1986). For example when toluene solutions of the known compound of spiro-indoline-oxazine structure (VIII) are exposed to a light source in the presence of an equimolecular quantity of benzophenone or anthraquinone, an inhibition effect on photochromatic activity is noted, as shown in graphs 1, 4 and 5 of FIG. 2. Specifically, graph 4 of FIG. 2 shows respectively the transmittance curves of the deactivated form and the form at maximum activation of the compound (VIII) and of the compound (VIII) with an equimolecular quantity of benzophenone. Graph 5 of FIG. 2 shows respectively the transmittance curves of the deactivated form and the form at maximum activation of the compound (VIII) and of the compound (VIII) with an equimolecular quantity of anthraquinone. Surprisingly, the $10^{-3}$M toluene solutions of compounds (IA) and (IB) under the same experimental conditions (FIG. 1) show high activation kinetics and a high coloration (transmittance variation), in contrast to those of the known compound (VIII) in the presence of benzophenone and anthraquinone. In addition the compounds of the present invention act as photosensitizers for example for known photochromatic compounds. Graph 6 of FIG. 3 shows respectively the transmittance curves for for $2.10^{-4}$M toluene solutions at maximum activation of the known compound (IX):

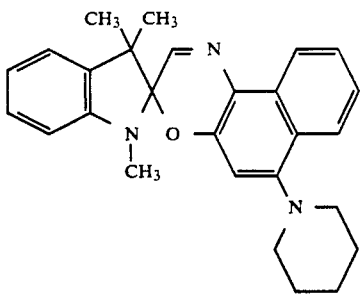

and of the compound (IB) of the present invention. Graph 7 of FIG. 3 shows respectively the theoretical transmittance curve at maximum activation for a 1:1 mixture of the compounds (IX) and (IB) and the experimental curve at maximum activation for the same mixture. Surprisingly the experimental transmittance curve shows much lower transmittance values than the theoretical, and consequently a much higher photochromatic effect than expected. The compounds (I) of the present invention demonstrate high photochromatic activity even on irradiation with visible light sources and hence with sunlight, with high activation and deactivation rates. Activation of the compounds (I) can in fact be obtained with a flash of visible light, such as that of photocopier machines, generally between 450 and 550 nm. This characteristic means that the compounds (I) of the present invention can be used as security markers for confidential documents. In addition the high activation/deactivation rate and stability of the compounds (I) enables transparent optical materials such as lenses, ophthalmic lenses, contact lenses, sunglasses, windows for vehicles and transport means in general, and windows in the building sector. The compounds (I) of the present invention are particularly useful for conferring photochromatic characteristics on articles of polymer materials used as solar filters, optical articles, optical memories, prints, photographs, fabrics, decorative articles and toys. The compounds (I) can be applied to the surface or incorporated in the required articles, by suitable methods. Certain photochromatic polymers can be obtained by dispersing the photochromatic compound homogeneously within the polymer mass and molding (e.g. by injection, compression and the like). Alternatively the photochromatic compound can be dissolved in a suitable solvent together with a polymer (such as polymethyl methacrylate, polyvinyl alcohol, polyvinyl butyral, cellulose butyrate acetate, epoxy, polysiloxane or urethane resin etc.) and deposited on a transparent support to form a photochromatic coating after evaporating the solvent. Again, the photochromatic compound can be added to a polymerizable monomer such as methyl methacrylate, so that after polymerization conducted in the presence of a suitable initiator such as azobisisobutyronitrile, they remain uniformly incorporated in the formed resin. According to a further method, the photochromatic compound can be dissolved in a suitable solvent in the presence of a resin, as heretofore described, this solution then being used to form a photochromatic film or sheet containing the uniformly dispersed photochromatic compound, by evaporating the solvent. Finally, the photochromatic compound can be applied to a transparent substrate (such as polycarbonate, polymethyl methacrylate, or polydiethyleneglycol bis(allyl carbonate)) by surface impregnation, effected by bringing the substrate into contact at a suitable temperature with a solution or dispersion containing the photochromatic compound.

The following experimental examples are provided to better illustrate the present invention.

EXAMPLE 1

Preparation of 3-hydroxy-4-nitroso-benzo[a]anthracene-7,12-dione

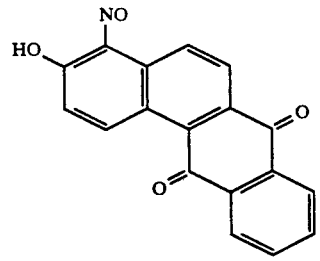

A solution of sodium hydroxide (0.72 g) in water (0.72 g) is added under stirring at ambient temperature to a suspension of 3-hydroxy-benzo[a]anthracene-7,12-dione, prepared as described in Journal Organic Chemistry (1986) 51 page 3502, (5 g; 18 mmoles) in butanol (25 ml). N-butylnitrite (2 g; 19.4 mmoles) is added over a period of 1 hour to the mixture, which is maintained at 60° C. The reaction mixture is maintained at 60° C. for 4 hours, cooled to ambient temperature and filtered. The solid is washed with toluene (2×10 ml), dried under vacuum and suspended in water (25 ml). Acetic acid (2 ml) is added to the suspension over a period of 30 minutes, operating at ambient temperature under stirring.

The suspension is kept stirred at ambient temperature for a further hour and then filtered. The solid is washed with water (3×20 ml) and dried under vacuum. In this manner 4.5 g of the required compound of the title are obtained, with sufficient purity for use in the next reaction.

EXAMPLE 2

Preparation of 1,3,3-trimethyl-spiro-indoline-2,3'-[3H]-benzo[a]anthracene-7',12'-dione(3,4-b)-1,4-oxazine (IB)

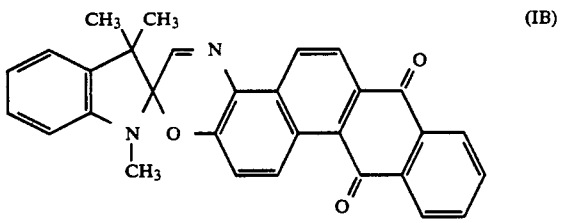

1,3,3-trimethyl-2-methylene-indoline (2.08 g; 12 mmoles) is added under stirring at ambient temperature to a suspension of 3-hydroxy-4-nitroso-benzo[a]anthracene-7,12-dione (4.4 g; 14.5 mmoles) in toluene (60 ml). The mixture is heated to 70° C. for 3 hours, then cooled to ambient temperature, diluted with toluene (60 ml) and washed with 3% aqueous hydrochloric acid, and finally dried with sodium sulphate. After evaporating the solvent under vacuum a crude product is obtained which on silica gel chromatography (eluent toluene)

provides 1 g of the required product of the title. Melting point 234.5° C. (DSC).

$^1$H-NMR (200 MHz, CDCl$_3$-TMS) δ (ppm): 1.35 (3H, s), 1.36 (3H, s), 2.77 (3H, s, NCH$_3$), 6.6–9.6 (13H, m).

Mass (m/e): 458.

Elemental analysis: Calculated: C 78.6%; H 4.8%; N 6.1%; Found: C 78.1%; H 4.7%; N 5.9%.

EXAMPLE 3

Preparation of 6-hydroxy-5'-nitroso-2'-naphthyl phenyl ketone

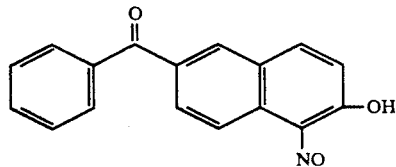

A solution of sodium hydroxide (0.16 g) in water (0.16 g) is added under stirring at ambient temperature to a suspension of 6-hydroxy-2'-naphthyl phenyl ketone, prepared as described in Journal of Am. Chem. Soc. (1950) 72 page 3215, (1 g; 4 mmoles) in n-butanol (5 ml). N-butylnitrite (0.42 g; 4 mmoles) is added over a period of 1 hour to the mixture, which is maintained at 60° C. The reaction mixture is maintained at 60° C. for 4 hours, cooled to 0° C. and filtered. The solid is washed with ethyl ether, dried under vacuum and suspended in water (5 ml). Acetic acid (0.5 ml) is added to the suspension over a period of 30 minutes, operating at ambient temperature under stirring. The suspension is kept stirred at ambient temperature for a further hour and then filtered. The solid is washed with water and dried under vacuum. In this manner 0.8 g of the required compound of the title are obtained, with sufficient purity for use in the next reaction.

EXAMPLE 4

Preparation of 1,3,3-trimethyl-8'-oxophenyl-spiro-indoline-2,3'-[3H]-naphtho(2,1-b)-1,4-oxazine (IA)

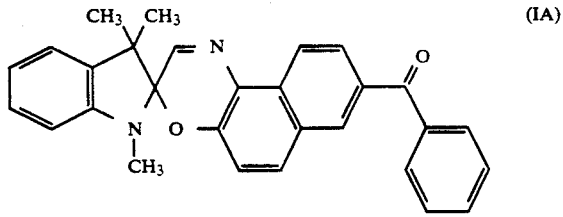

1,3,3-trimethyl-2-methylene-indoline (1.06 g; 6.1 mmoles) is added under stirring at ambient temperature to a suspension of 6'-hydroxy-4-nitroso-2'-naphthyl phenyl ketone (1.7 g; 6.1 mmoles) in toluene (30 ml). The mixture is heated to 70° C. for 6 hours, then cooled to ambient temperature, diluted with toluene (30 ml) and washed with 3% aqueous hydrochloric acid, and finally dried with sodium sulfate. After evaporating the solvent under vacuum a crude product is obtained which on silica gel chromatography (eluent hexane:ethyl acetate, 5:1 by volume) provides 0.9 g of the required product of the title. Melting point 180° C. (DSC).

$^1$H-NMR (200 MHz, CDCl$_3$-TMS) δ (ppm): 1.34 (3H, s), 1.36 (3H, s), 2.76 (3H, s, NCH$_3$), 6.5–8.6 (15H, m).

Mass (m/e): 432.

Elemental analysis: Calculated: C 80.6%; H 5.6%; N 6.6%; Found: C 79.9%; H 5.6%; N 6.3%.

EXAMPLE 5

Preparation of 1,3,3-trimethyl-8'-oxophenyl-6'-piperidinyl-spiroindoline-2,3'-[3H]-naphtho(2,1-b)-1,4-oxazine (IC)

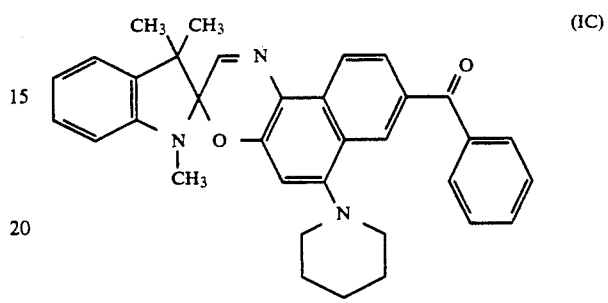

Piperidine (0.21 ml; 2.17 mmoles) is added under stirring at ambient temperature to a suspension of 6'-hydroxy-4-nitrosophenyl ketone (0.6 g; 2.17 mmoles) in toluene (8 ml). The reaction mixture is heated to 70° C. for 30 minutes. The resultant solution is added to a solution of 1,3,3-trimethyl-2-methyleneindoline (0.187 g; 1.08 mmoles) in toluene (2 ml) mantained at 70° C. The reaction mixture is maintained at 70° C. for 3 hours, then cooled to ambient temperature, diluted with toluene (90 ml) and washed with 3% aqueous hydrochloric acid (100 ml), and finally dried with sodium sulfate. After evaporating the solvent under vacuum a crude product is obtained which on silica gel chromatography (eluent toluene) provides the required product of the title.

$^1$H-NMR (200 MHz, CDCl$_3$-TMS) δ (ppm): 1.35 (6H, s), 1.35 (2H, m), 1.58 (4H, m), 2.75 (3H, s, NCH$_3$), 3.02 (4H, m), 6.6–8.7 (14H, m).

Mass (m/e): 501.

Elemental analysis: Calculated: C 81.4%; H 6.6%; N 5.6%; Found: C 81.0%; H 6.7%; N 5.4%.

We claim:

1. A photochromatic and photosensitizing composition comprising a spiro-indoline-oxazine of the general formula (I):

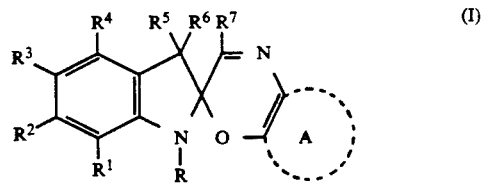

where
R represents a methyl group; a C$_1$–C$_5$ carboxyalkyl group; a cyano group; or a C$_2$–C$_5$ alkenyl group;
R$^1$ to R$^4$, which can be identical or different, each independently represent a hydrogen atom; a linear or branched C$_1$–C$_5$ alkyl group; a C$_1$–C$_5$ alkyl group substituted with 1 to 5 atoms of halogen chosen from fluorine, chlorine, bromine and iodine, hydroxy groups, C$_1$–C$_5$ alkoxy groups, C$_1$–C$_5$ carboxyalkyl groups, cyano groups; a C$_2$–C$_5$ alkenyl group, a benzyl group, a halogen atom chosen from fluorine, chlorine, bromine and iodine; a hydroxy group; a $C_1$-$C_5$ alkoxy group; an amino group; a $C_1$-$C_5$ monoalkyl amino group; a $C_1$-$C_5$ dialkyl amino group; a $C_3$-$C_{10}$ cycloalkyl amino group; a piperidino, piperazino or morpholino group; a carboxyl group; a $C_1$-$C_5$ carboxyalkyl group; a $C_2$-$C_5$ carboxyalkenyl group; a carboxyamide group; a $C_1$-$C_5$ N-alkyl substituted carboxyamide group; a $C_1$-$C_5$ N,N-dialkyl substituted carboxyamide group; a cyano group; a nitro group; a sulfonic group; a $C_1$-$C_5$ alkylsulfonic group; an arylsulphonic group chosen from benzenesulfonic, p-toluenesulfonic and p-chlorotoluenesulfonic groups; or an aryl group chosen from phenyl, diphenyl and naphthyl groups;

$R^5$ and $R^6$ both represent a methyl group;

$R^7$ represents a hydrogen atom; or a halogen atom chosen from fluorine, chlorine and bromine; and A represents a monocyclic or polycyclic arene group containing at least one carbonyl function (C=O) on the nucleus or in a side chain, and chosen from those representable by the following formulas (II), (III), (IV), (V) or (VI):

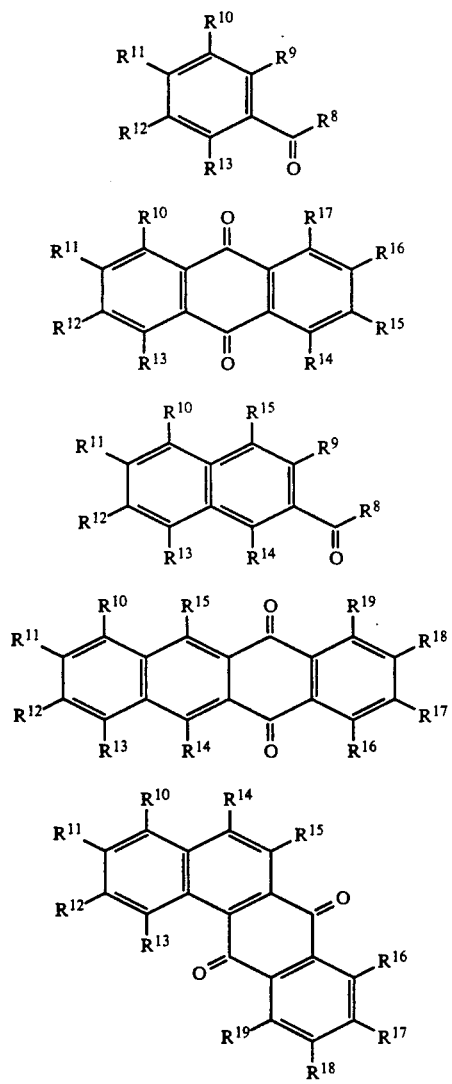

where $R^8$ represents a hydrogen atom; a halogen atom chosen from chlorine and bromine; a linear branched $C_1$-$C_5$ alkyl group; a $C_2$-$C_5$ alkenyl group; a monocyclic or polycyclic aryl group; or a heteroaryl group chosen from phenyl, naphthyl, anthracyl, furanyl, thiophenyl, quinolyl and pyrrolyl; or an aryl or heteroaryl group substituted with 1 to 4 groups chosen from a halogen atom selected from fluorine, chlorine and bromine, linear or branched $C_1$-$C_5$ alkyl groups, hydroxy groups, $C_1$-$C_5$ alkoxy groups, nitro groups, cyano groups, amino groups, $C_1$-$C_5$ monoalkyl amino groups; $C_1$-$C_5$ dialkyl amino groups; piperidino groups, piperazino groups or morpholino groups;

two adjacent of $R^{10}$ to $R^{13}$ represent the position of fusion with the oxazine ring in general formula (I), the others having the same meaning as $R^9$ and $R^{14}$-$R^{19}$;

$R^9$ and $R^{14}$-$R^{19}$ represent a hydrogen atom; a linear or branched $C_1$-$C_5$ alkyl group; a $C_1$-$C_5$ alkyl group substituted with 1 to 5 atoms of halogen chosen from fluorine, chlorine, bromine and iodine, hydroxy groups, $C_1$-$C_5$ alkoxy groups, $C_1$-$C_5$ carboxyalkyl groups, cyano groups; a $C_2$-$C_5$ alkenyl group; a benzyl group; a halogen atom chosen from fluorine, chlorine and bromine and iodine; a hydroxy group; a $C_1$-$C_5$ alkoxy group; a carboxyl group; a $C_1$-$C_5$ carboxyalkyl group; a $C_1$-$C_5$ carboxyalkenyl group; a carboxyamide group; a $C_1$-$C_5$ N-alkyl substituted carboxyamide group; a $C_1$-$C_5$ N,N-dialkyl substituted carboxyamide group; a cyano group; a nitro group; a sulfonic group; a $C_1$-$C_5$ alkylsulfonic group; an arylsulfonic group chosen from benzenesulfonic, p-toluenesulfonic and p-chlorotoluenesulfonic groups; or an aryl group chosen from phenyl, diphenyl and naphthyl groups.

2. (Amended) A composition as claimed in claim 1, wherein in formula (I):

R represents a methyl, 2-allyl or 2-carboxymethylethyl group;

$R^1$-$R^4$, which are identical or different, each independently represent a hydrogen atom, a fluorine, chlorine or bromine atom, or a methyl, isopropyl, trifluoromethyl, hydroxymethyl, benzyl, hydroxy, methoxy, amino, piperidino, morpholino, carboxyl, carboxymethyl, N,N-dimethylcarboxyamide, cyano, nitro or phenyl group;

$R^5$ and $R^6$ both represent a methyl group;

$R^7$ represents a hydrogen atom or a chlorine atom;

A is one of the groups of formulas (II) to (VI) in which:

$R^8$ represents a hydrogen atom, or a methyl, isopropyl, phenyl, p-N,N-dimethyl aminophenyl, p-cyano phenyl, p-nitro phenyl, p-methoxy phenyl, naphthyl, 2-thiophenyl, 2-furanyl or 4-pyridyl group;

two adjacent of $R^{10}$-$R^{13}$ represent the position of fusion with the oxazine ring in general formula (I), the others then each independently representing a hydrogen atom, a fluorine, chlorine or bromine atom, or a methyl, isopropyl, trifluoromethyl, hydroxymethyl, benzyl, hydroxy, methoxy, carboxyl, carboxymethyl, N,N-dimethylcarboxyamide, cyano, nitro or phenyl group;

$R^9$ and $R^{14}$ to $R^{19}$ each independently represent a hydrogen atom, a fluorine, chlorine or bromine atom, or a methyl, isopropyl, trifluoromethyl, hydroxymethyl, benzyl, hydroxy, methoxy, carboxyl, carboxymethyl, N,N-dimethylcarboxyamide, cyano, nitro or phenyl group.

3. A photochromatic and thermochromatic composition according to claim 1, selected from the group consisting of:

1,3,3-trimethyl-8'-oxophenyl-spiro-indoline-2,3'-(3H)naphtho-(2,1-b)-1,4-oxazine; and 1,3,3-trimethyl-spiro-indoline-2,3'-(3H)benzo(a)anthracene-7',12'-dione(3,4-b)-1,4-oxazine.

4. A photochromatic and thermochromatic composition as defined in claim 1 comprising:

1,3,3-trimethyl-8'-propionyl-spiro-indoline-2,3'-(3H)naphtho-(2,1-b)-1,4-oxazine.

* * * * *